United States Patent [19]

Allen et al.

[11] Patent Number: 4,999,287
[45] Date of Patent: Mar. 12, 1991

[54] DIRECT MEASURING ASSAY STRIP AND METHOD OF USE THEREOF

[75] Inventors: Michael P. Allen, Sunnyvale; Robert B. Shibuya, Los Altos, both of Calif.

[73] Assignee: Chemtrak Corporation, Sunnyvale, Calif.

[21] Appl. No.: 195,881

[22] Filed: May 19, 1988

[51] Int. Cl.$^5$ ............ C12Q 1/28; C12Q 1/54; C12Q 1/60; G01N 21/78
[52] U.S. Cl. ................................ 435/11; 422/56; 422/58; 422/61; 435/14; 435/25; 435/28; 435/805; 435/810; 436/169
[58] Field of Search ............ 436/169, 805, 817; 422/56, 58, 60, 61; 435/11, 14, 805, 810, 25, 28

[56] References Cited

U.S. PATENT DOCUMENTS

| | | | |
|---|---|---|---|
| 3,511,608 | 5/1970 | Anderson | 422/56 |
| 3,893,808 | 7/1975 | Campbell | 422/56 |
| 4,108,729 | 8/1978 | Mennen | 422/56 |
| 4,826,759 | 2/1989 | Guire et al. | 422/57 |
| 4,861,711 | 8/1989 | Friesen et al. | 422/56 |
| 4,876,067 | 10/1989 | Deneke et al. | 422/58 |

Primary Examiner—Robert J. Hill, Jr.
Attorney, Agent, or Firm—Bertram I. Rowland

[57] ABSTRACT

Methods and compositions are provided for measuring an analyte without instrumentation. The device employs a stripstick which may include as its components, a discontinuous flow path, which is made continuous after transfer of the sample, means for automatically metering the volume of a sample, and means for providing a sharply delineated color front. The method finds particular use where a limited amount of substrate is provided for an enzyme on a sample pad.

21 Claims, 8 Drawing Sheets

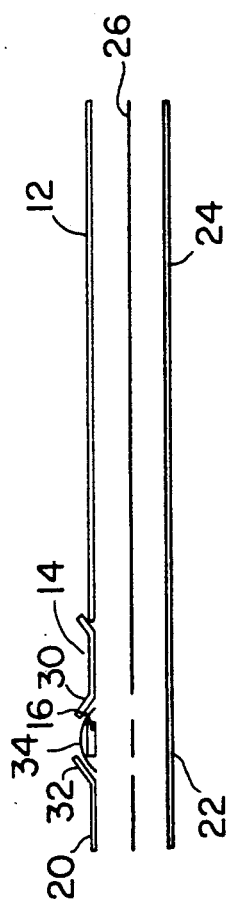

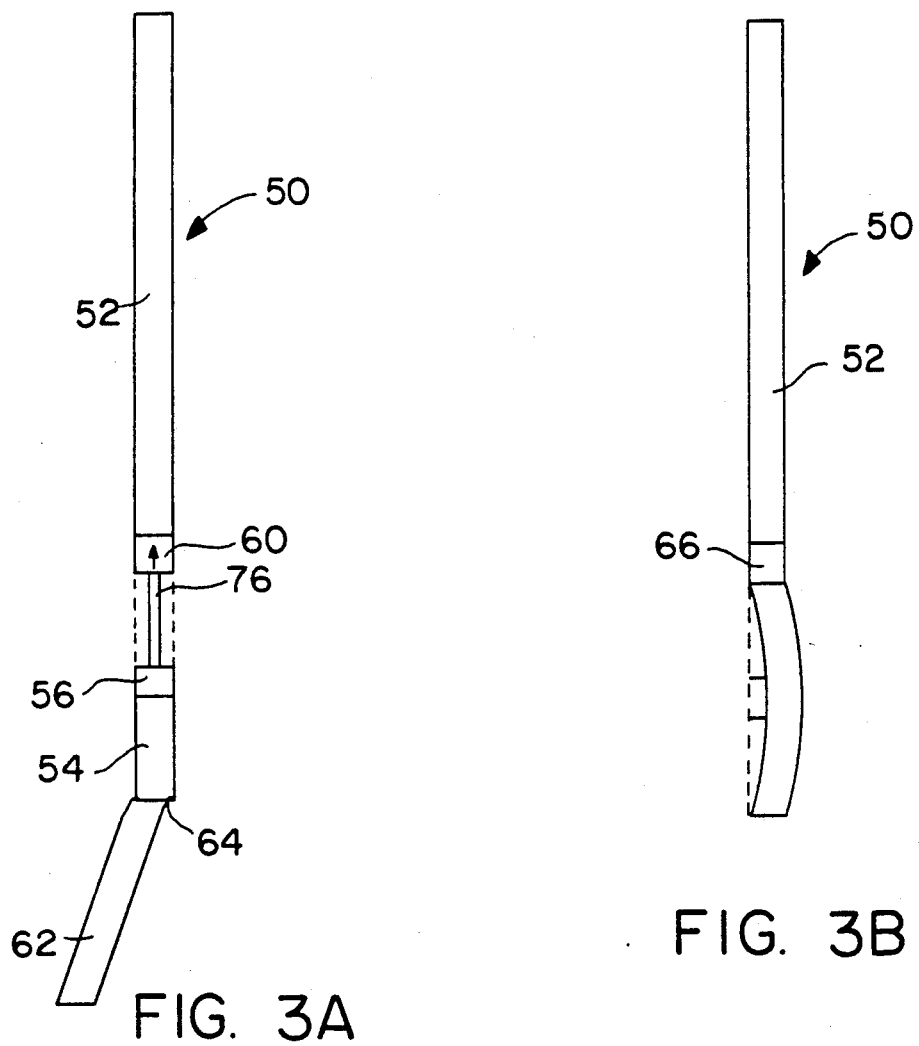

DIRECT MEASURING ASSAY STRIP AND METHOD OF USE THEREOF

TECHNICAL FIELD

The field of the subject invention concerns diagnostic assay strips permitting visual measurement.

BACKGROUND

The ability to measure a wide variety of physiologically active compounds, both naturally occurring and synthetic, has become of increasing importance, both as an adjunct to diagnosis and therapy. While for the most part, assays of physiological fluids and drugs have required clinical laboratory determinations, there is an increasing awareness of the importance of being able to carry out assay determinations in the doctor's office and in the home. To be able to perform an assay in a doctor's office or home requires that an assay have a simple protocol and be relatively free of sensitivity to small changes in the conditions under which the assay is carried out. Importantly, accurate measurements of reagents and sample should whenever feasible be avoided. Numerous systems have been developed in efforts to try to address the various problems associated with analysis outside of the clinical laboratory. There is, nevertheless, a continuing interest in providing improved and alternative methods to those which are presently generally available.

Exemplary of this situation is the need today to be able to determine cholesterol levels or low density protein levels in blood. There is a clearly established relationship between total blood cholesterol (mainly LDL fraction) and coronary artery disease (Journal of the American Medical Association (1985) 253:2080–2086). New guidelines have been established for adults over 20 years of age to identify risk groups associated with blood cholesterol level. These levels are as follows: <200 mg/dl is a desirable blood cholesterol; 239 mg/dl is borderline high blood cholesterol; >240 mg/dl is high blood cholesterol.

Cholesterol levels can be controlled by both diet and cholesterol lowering drugs. The key is to identify those individuals at risk. By being able to monitor one's own cholesterol at home for those individuals at risk will provide a significant tool in monitoring cholesterol levels and reducing the potential for heart disease. The measuring of other naturally occurring compounds of physiologic importance and synthetic drugs is also of great interest.

Relevant Literature

Demacker et al., *Clin. Chem.* (1983) 29:1916–1922 reports the evaluation of cholesterol assay kits. Studies associated with enzyme assays include Gochman and Schmitz, *Clin. Chem.* (1971) 17:12; Paul, *The Enzymes* (1963) 8:227–274; *Current Status of Blood Cholesterol Measurement in Clinical Laboratories in the United States: A Report from the Laboratory Standardization Panel of the National Cholesterol Education Program* (1988) 34(1):193-201; and U.S. Pat. Nos. 4,391,904; 4,366,241; 4,168,146; 4,435,504; 4,533,629; 4,540,659, and references cited therein. See also, copending Application Ser. No. 064,883, filed June 22, 1987.

SUMMARY OF THE INVENTION

Diagnostic strips are provided which permit the determination of a variety of analytes, particularly analytes which are enzyme substrates. The strips provide for a visual determination of the amount of the analyte, comprising as subcomponents a sample pad which permits substantially quantitative measurement of the sample to be determined, an interrupted flow path completed by the sample pad, and a strip configuration which provides for the formation of a rocket-shaped color front, for easy detection of the analyte level.

BRIEF DESCRIPTION OF THE DRAWINGS

FIG. 2 is an exploded elevational side view of an assay strip;

FIGS. 3a and 3b are plan views of an alternative embodiment of a strip, FIG. 3a being an exposed view and FIG. 3b the configuration for use, while

DESCRIPTION OF THE SPECIFIC EMBODIMENTS

Figure 1A:
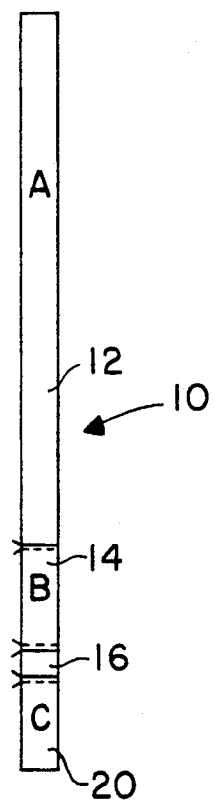
FIGS. 1a and 1b are front and rear plan views of a diagnostic strip.

Methods and apparatus are provided for the detection of analytes employing diagnostic strips which allow for a visual determination of an amount of analyte present in a sample. The method employs a sample pad which becomes impregnated with the sample resulting in the presence of a product in proportion to the amount of analyte in the sample. The product is then transported from the sample pad through a bibulous strip onto another bibulous strip impregnated with signal-forming reagents. A dual-stream path may be provided, one stream path being directed through the sample pad; and a second stream path bypassing the pad, where the sample pad stream path is a narrower path than the diverted path. The two paths meet in the bibulous strip measuring or quantitation region, resulting in a sharply delineated rocket formation color front. The height of the color front may be related to the amount of analyte in the medium.

In carrying out the assay, a sample may or may not be subjected to pre-treatment. The sample is spotted onto the sample pad. Where the sample pad is to serve as the sample volume measuring device, the pad will have one side exposed for receiving the sample and the other side in contact with a porous, non-wettable film which is in contact with an absorbant layer. The sample will saturate the sample pad and any residual fluid will overflow through the porous film and be absorbed by the absorbant layer. In this way, a fixed amount of sample fluid will be taken up by the pad. The pad may be impregnated with reagents, which together with the sample and, as appropriate, components in the transport medium will result in an enzymatic reaction producing a product. Alternatively, the product may be produced prior to adding the sample solution to the pad and added as part of the sample. This product will be transported by the transport medium through a bibulous layer impregnated with a signal-producing compound, which will react with the product to produce a signal, usually the creation or loss of color, defining a boundary. By virtue of having two streams, a rocket-shaped boundary or front is achieved which is readily detectable and easily measured.

Any analyte may be determined. However, analytes may be divided into two categories. The first category includes those analytes which may serve as a substrate for an enzyme, resulting in a product which can further react with another compound to produce a detectable product, particularly a visually colored product. These compounds may be illustrated by galactose, glucose, or other saccharides, cholesterol, urea, nicotinamide adenine dinucleotide, riboflavin, compounds which result in the reduction or oxidation of co-factors, such as NAD or NADP (D.L. Morris et al., Third European Congress of Clinical Chemistry, Brighton, England, June 1979).

For those analytes which result in the production of hydrogen peroxide, namely those compounds which, for the most part, are associated with oxidases, the resulting hydrogen peroxide may react in the presence of a peroxidase, e.g. horseradish peroxidase (HRP), with a wide variety of horseradish peroxidase substrates. These substrates include 0-chlorophenol benzidine, tetramethylbenzidine, dimethylaniline in conjunction with 3-methyl-2-benzothiazolinone hydrazone (MBTH), dicarboxidine, 0-dianisidine, 4-chloro-1-naphthol, etc. The compounds which are bound to the assay measurement region may react by themselves with the enzyme product or in conjunction with a component in the transport medium.

Where various reductants are produced, such as NADH, FMNH, etc., compounds which may be bound in the assay measurement region may include methylene blue, N-methyl phenazine methosulfate, ferrocene, ferridoxin, cytochrome c, triphenyltetrazolium, etc., preferably where the reduced compound is colored.

The other format will involve those analytes which are not substrates of enzymes which produce a product which can be used to form a detectable signal by reacting with another substance. These analytes can be employed in a variety of ways where the analyte or analyte analog is joined to another compound which serves to modulate enzyme activity. For example, co-enzyme conjugates can be prepared where the co-enzyme conjugate will compete with the analyte for antibody to the analyte. The antibody bound conjugate will be unable to bind to the enzyme and no reaction will occur. Free co-enzyme conjugate will be able to bind and allow for a single reaction in the absence of a regeneration system.

Similarly, the analyte may be conjugated to a substrate for the enzyme, where the substrate provides a product analogous to the products described previously, which react with the compound in the assay measurement region. To enhance sensitivity, one may provide for a polysaccharide linked to an analyte analog, where the sample pad will include an enzyme which will degrade the polysaccharide and provide a plurality of substrate molecules for the saccharide oxidase. In this situation, where an antibody does not block the reaction, a heterogeneous format may be used, where the analyte and conjugate compete for a limited amount of antibody bound to a surface and the supernatant is then the sample which is applied to the pad. In this case, some measurement will be required to ensure the proper amount of sample as well as buffer.

The subject method and device can be used to monitor any solution comprising a first compound, which by itself or by enzymatic transformation will react with another compound to produce a signal resulting in a detectable boundary in the measurement region. Therefore, any methodology which provides such a first compound can be monitored. By using a plurality of determinations, rate measurements can be made, where the reaction does not continue in a significant manner once transferred to the sample pad. Alternatively, one could terminate the reaction so that no further reaction occurs and then use the solution for impregnating the sample pad. In this manner both "homogeneous" and "heterogeneous" enzyme immunoassays, enzyme assays, or the like may be performed, where the device serves only as a metering or measuring instrument.

Any analyte may be employed, regardless of its size and nature, by employing the appropriate protocol. The analytes may be haptens or antigens, will usually be of at least about 32 MW and may be 1,000,000 MW or more, may involve naturally-occurring compounds, synthetic compounds, or combinations thereof. The compounds may vary from methanol to high molecular weight proteins comprising a plurality of subunits. The compounds may be monomeric or polymeric. A long list of analytes is provided in U.S. Pat. No. 4,261,968, which disclosure is incorporated herein by reference.

Categories of analytes of particular interest will be those analytes involving synthetic drugs, particularly those employed with chronic diseases, such as valproate, theophylline, barbiturates, etc., drugs of abuse, and the like. Other compounds of interest will be those which are naturally occurring, particularly physiologically active compounds, such as hormones, growth factors, colony stimulating factors, interferons, surface membrane proteins, viral proteins, animal proteins, antibodies, enzymes, etc., both proteinaceous and non-proteinaceous. The conjugates which are prepared, may be prepared in conventional ways, and will vary with the particular component which interacts with the enzyme and the nature of the analyte. A wide variety of linking groups are known and can be used and will be chosen so as to minimize the inhibition of the reaction with the enzyme and maximize the inhibition by the antibody, where a homogeneous system is employed.

The subject method may be employed in any situation where a fixed amount of a substance is involved, which can be transferred to the sample pad for measurement or further reaction and reacts with another compound to produce a detectable boundary. These types of assays may be illustrated by ELISA assays, EMIT assays, sandwich assays, or the like.

Depending upon the protocol, the sample pad to which the sample is added may be prepared in a variety of ways. It may be untreated, impregnated with buffer, or provide a reagent signal-producing system. A variety of sophisticated reagents, protocols or regimens can be devised based on a limited amount of material migrating to produce a boundary in proportion to the amount of material present. Examples of protocols would include particles having first and second ligands, where the first ligand competes with analyte for receptor bound to a surface. After carrying out the competition for a limited amount of receptor between analyte and particle, an aliquot of the assay medium is transferred to the sample pad and the particle transported with eluent through the measurement region. By having receptor for the second ligand in the measurement region, the particle boundary will be defined by the number of particles added to the pad. By having colored particles, charcoal particles, magnetic particles, dyes, dye-polymer conjugates, proteins with high visible extinction coefficients, e.g.

phycobiliproteins, or the like, the boundary will be readily defined.

Any technique which allows for binding of a detectable entity in proportion to an analyte of interest may be employed. These may include cleavage of a bond to release the entity, where the bond to the entity is not cleavable when the entity is bound to a receptor, binding to a support which inhibits migration of the entity in proportion to the amount of analyte in a sample, or the like. The entity may be a particle as described above, an enzyme which catalyzes the production of a detectable product, or the like.

Of particular interest is where a product is produced on the sample pad which provides for a detectable boundary. For example, where the analyte is a substrate, the sample pad may be impregnated with the appropriate enzyme or enzymes to provide for a product. Normally, the enzyme product will react, either directly or indirectly, with a compound which is fixed in the assay measurement region. This may be exemplified by cholesterol, glucose, or the like, which react with an oxidase to provide an oxidizing species. The oxidizing species may then react with the bound compound or a mobile compound which reacts with the bound compound to produce a detectable boundary. Illustrative of this situation would be the hydrolysis of serum cholesterol ester by cholesterol esterase (EC:3.1.1.13) and subsequent oxidation of cholesterol by cholesterol oxidase (EC:1.1.3.6) to produce a stoichiometrically identical amount of $H_2O_2$. This $H_2O$'is formed in a stationary reaction pad and combines with HRP which is in the mobile phase. The $HRP.H_2O_2$ reacts with a bound substrate to produce a detectable boundary.

Depending upon the assay, other reagents may also be present. For example, detergents find use where a lipophilic analyte in blood is involved, where the lipophilic analyte binds to proteins present in the blood. This may be illustrated by cholesterol which binds to proteins, as for example in very low, low and high density lipoproteins. Thus, detergents such as non-ionic, anionic, or cationic detergents may be employed. Of particular interest are polyoxyalkylenes, ethoxylated alkylphenols, octylphenoxypolyethoxyethanol, octylphenol-ethylene oxide condensates and polyoxyethylene lauryl ethers, or anionic detergents, such as bile acids, e.g. sodium cholate and sodium taurocholate. In addition, various sticking agents or adhesives may be employed, such as gum arabic. Also of interest will be proteins which are substantially noninterfering, which may include gelatin, casein, serum albumin, or gamma globulins. In addition, the reagent pad may include preservatives, such as sucrose, polyvinyl alcohol, polyvinyl pyrrolidone, dextran or sodium azide. Finally, a buffered solution will normally be employed for impregnating the pad, where any convenient buffer may be employed, generally a substantially dilute buffer, which may include phosphate, tris, MOPS, borate, carbonate, or the like. Usually, the buffered solution will be at a pH in the range of about 4 to 9. The buffer concentration will generally be from about 10 to 500 mM.

In the case of the cholesterol assay as illustrative of other assays, the impregnating solution will have from about 2 to 100 units/ml of the two enzymes, cholesterol esterase and cholesterol oxidase. The detergents will be in total weight from about 0.1 to 5 weight percent of the medium, while in the case of mixtures the weight of the non-ionic detergents may be from about 10 to 90%, usually from about 25 to 75 weight percent of the total detergent mixture. The binding agents or adhesives will generally be in the range of about 0.2 to 10, more usually from about 1 to 5 weight percent of the medium. A preservative or hydrogen bonding agent may be present in from about 1 to 20 weight percent, more usually from about 2 to 10 weight percent. The remaining additives will generally be present in total amount in less than about 10 weight percent, more usually in less than about 5 weight percent. The remaining composition may be water, non-reactive ingredients, excipients, extenders, and the like.

The assay is carried out by impregnating a sample pad which serves as a bridge between two bibulous members. A first bibulous member serves to receive the transport solution, which may or may not have reaction components, depending upon the assay. The first bibulous member transfers the fluid to the sample pad. The second bibulous member receives the transport fluid from the sample pad and serves as a bridge to transfer the transport fluid from the sample pad to the assay measurement region. The sample is prevented from interacting with the two bibulous members when sample is transferred to the pad by a separation means, usually an inert non-porous film, which blocks transfer from the sample pad to the bibulous members. The amount of sample accepted by the sample pad and involved in the assay medium may be controlled by providing for transfer of fluid beyond the amount saturating the pad through a non-wetting screen into an absorbant layer. After addition of the sample to the sample pad, and an incubation of from 1 to 30 minutes, the porous non-wetting material and absorbant layer are removed, leaving the sample pad as the sole repository of sample for the assay.

A transport fluid is provided whose path is bifurcated, where the path between the sample pad and the assay measurement region is narrower than a second path for the transportation medium which meets the transportation medium from the assay sample pad. Thus, the transport medium carrying the migratable components from the sample pad and the transport medium which does not include the component(s) from the sample pad meet and mix, where the signal-producing or color-producing component is directed along a central path in the assay measurement region and does not have significant diffusion toward the sides of the assay measurement region strip. In this manner, a rocket conformation is achieved whereby there is a sharp delineation at the detectable boundary between a region providing a detectable signal, e.g. color, and a region lacking such signal, without migration along the edges, a fuzzy undefinable front, nor a difficultly defined meniscus.

Figure 1B:
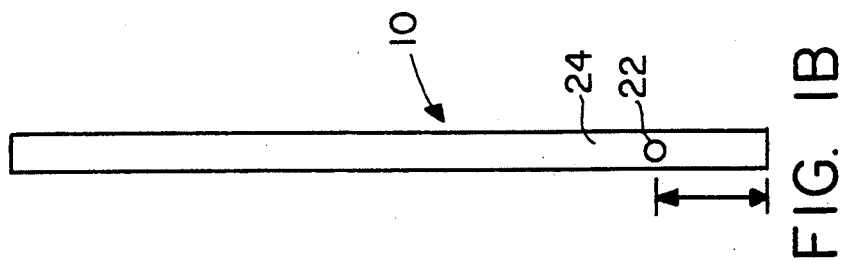

For further understanding of the invention, the drawings will now be considered. In FIGS. 1a and 1b, an embodiment is shown which is primarily directed to an interrupted flow method to prevent the transfer of any sample away from the sample pad to bridging bibulous strips. In FIG. 1a, the assay strip 10 has an assay measurement or quantitation area 12 to which is adhered a bibulous strip 14 which extends from the quantitation area 12 to the sample pad 16. The bibulous strip 14 overlaps the sample pad 16 and provides for flow of a fluid from the sample pad 16 to the quantitation area 12. A second bibulous strip 20 extends from the sample pad 16 to the end of the strip for receiving fluid, transporting fluid or eluent, which will be transported from a fluid source to the sample pad 16.

In FIG. 1b a rear view is given of the strip 10 which shows a loading port 22 through support layer 24. The loading port 22 exposes sample pad 16. The support layer 24 is a fluid impervious layer which is present to provide for structural stability to the strip.

In FIG. 2, the top layer 12 is shown above support layer 24 and separated by adhesive layer 26 which bonds the quantitation area layer 12 to the support layer 24. Bibulous layers 14 and 20 are shown adhered to the support layer 24 by means of adhesive layer 26 and have elevated ends 30 and 32 respectively which overlap sample pad 16 and are prevented from contacting sample pad 16 by protective strip 34. Protective strip 34 is present at the time of fabrication of the assay strip and is removed after the sample is loaded onto sample pad 16 and sample incubation is complete.

The entire strip may have a length of about 25 to 200 mm, more usually from about 50 to 150 mm, preferably about 100 mm. About 25 to 90% of the length of the strip will be the measurement or quantitation area. The strips which provide for flow of fluid to and from the sample pad may be of the same or different length and will generally be from about 5 to 25, more usually about 10 to 20% each of the length of the strip. The sample pad will generally be from about 1 to 10%, more usually from about 2 to 8% of the length of the strip, the longer the strip, the larger the sample pad may normally be. The width of the strip may be varied widely, usually being at least about 3 mm and not more than about 10 mm, preferably from about 4 to 7 mm. The bridging strips will usually overlap the sample pad by at least about 0.2 mm and not more than about 2 mm, usually about 1 mm, being primarily a matter of convenience, so long as the bridging strips are not in direct fluid communication.

Any convenient material may be used for the various bibulous parts of the assay strip. Usually, the thickness of the bibulous components will be in the range of about 0.05 to 2.0 mm, more usually 0.15 to 0.75 mm. A wide variety of bibulous supports may be employed, particularly cellulosic supports, such as chromatography paper, silica on a support, alumina on a support, and polymeric membranes such as nitrocellulose and nylon. The characteristics of the bibulous material employed for the measurement region include the need in many instances to covalently or irreversibly bind an indicator molecule to the support, that the color developed should be clear and sharp, and that the fluid should be capable of flowing at a convenient rate through the bibulous member. In addition, the bibulous member should be able to adhere to a support, as well as allowing for adherence of the bridging bibulous member to the measurement region bibulous member without significant interference with flow from the bridging member to the measurement member.

The support layer may be any convenient rigid backing material, generally from about 0.002 to about 0.05, more usually from about 0.005 to 0.025 inch thick. A wide variety of rigid convenient materials are available, for the most part polymers, which include polystyrene, polyvinylacetate, polyvinylchloride, polyester, etc. The adhesive layer may be any convenient adhesive which does not significantly penetrate the bibulous member and interfere with flow. For the most part, double-stick tape adhesive has been found to be convenient and successful. Double-stick adhesives include 3M 415, 443, or 9460.

As already indicated, in carrying out the assay determination, the sample is introduced at the sample loading port 22 and is absorbed by the sample pad 16. After the sample has been completely absorbed and a defined incubation period has elapsed, the protective strip 34 is removed, at which time the elevated ends 30 and 32 of the bibulous strip bridging members 14 and 20 make contact with the sample pad 16. The bibulous strip bridging member 20 is now immersed in the transport fluid, whereby the fluid flows through the bridging member 20 through the pad carrying with it product or other substances (which will provide for signal production in the measurement area 12) through the bridging member 14 into the bibulous measurement area 12.

Figure 3C:
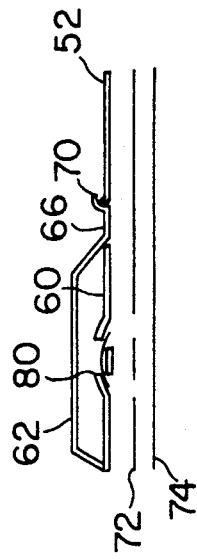
FIG. 3c is a side elevational view of an alternative embodiment.

The next embodiment, depicted in FIGS. 3a–c, is a preferred embodiment of the subject invention and employs a fluid flow conformation resulting in a sharp rocket-shaped color front and automatic means for providing a measured amount of sample associated with the sample pad. In this device, assay strip 50 has measurement or quantitation area 52 with bridging strip 54, sample pad 56 and bridging bibulous strip 76 extending to space 60. In addition, a spanning flow diversion strip 62 is provided which extends from the immersion end 64 of the assay strip device 50 over the bridging strip 54, pad 56, and fills space 60 to provide for continuity to measurement area 52. Spanning flow diversion strip 62 thus forms an intervening juncture in the plane of measurement region 52 and bridging strip 76, so as to provide a bibulous joining region 66, resulting in a continuous layer and flow path between bridging region 76 and measurement region 52. The end 70 of the flow diversion strip 62 may abut measurement region 52 or extend over the end of measurement region 52 to ensure smooth fluid flow.

As in the previous embodiment, an adhesive layer 72 firmly binds the bibulous strips to the support film 74. All or part of bibulous strip 76 is of narrower dimension than the measurement region 52 so as to provide a narrow neck 76 which results in the flow path from sample pad 56 being narrower than the flow path from flow diversion strip 62, as the two streams enter the measurement area 52. The result of having the sample stream narrower than the transport fluid stream when the two streams meet in the measurement area and the measurement area is wetted by the transport fluid is to maintain a relatively sharply defined color front to produce a rocket conformation which can be easily discriminated and measured. The bibulous bridging strip 76 may for example have a width in the range of about 2 to 4 mm, where the measurement area has a width of 5 mm. That is, the bridging strip will usually be at least 1 mm smaller than the measurement area, and may range from about 20 to 80% of the width of the measurement area. The diversion strip, on the other hand, will be about the width of the measurement area.

Figure 4:
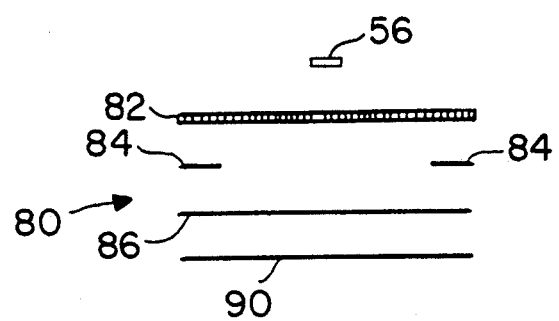
FIG. 4 is an exploded cross-sectional view of one embodiment of a metering device.

In addition, automatic measurement of the sample volume in the sample pad may be achieved by employing a metering device. The metering device substitutes for the protective strip 34 in the previous embodiment. In FIG. 4 is shown the metering device 80 which is comprised of the sample pad 56 which is shown above the screen 82, which in turn is bonded by means of adhesive strips 84 to absorbant 86. The adhesive strips 84 are distant from the region of the sample pad 56, so as to avoid interference with the transfer of fluid from the sample pad 56 to the absorbant 86. The absorbant 86 is covered with an inert film 90, which prevents transfer of fluid from the absorbant to the bridging strips 54 and 76.

The screen is characterized by having a mesh of from about 100 μm to about 1 mm, preferably from about 200 μm to about 500 μm. The thickness will generally be from about 150 μm to 600 μm, more usually from about 200 μm to 400 μm. The composition may be nylon, polyester, polyethylene, or the like, so long as the dimensions and composition do not allow continuity of capillary flow between the sample pad and the absorbant pad, but allows for wicking upon saturation of the sample pad. Conveniently, the sample pad may be of a dimension to have a volume capacity of from about 5 to 100 μl more usually from about 10 to 50 μl. By having a sample transferred to the pad greater than the capacity of the pad, saturation of the pad and transfer of excess sample to the absorbant layer can be assured, so that an accurate volume will be accepted by the pad. The volume administered to the pad may be as a single drop, or a plurality of drops.

The screen will be laid on top of the sample pad, so that it may be removed subsequently, when the strip end is immersed in the transport fluid.

Figure 5A:
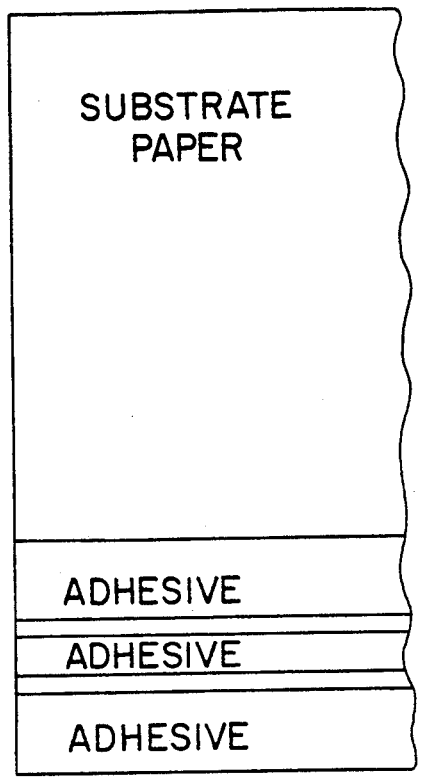
FIGS. 5a-f are diagrammatic views of the assembly of strips, with the substrate partially cut away.
Figure 5B:
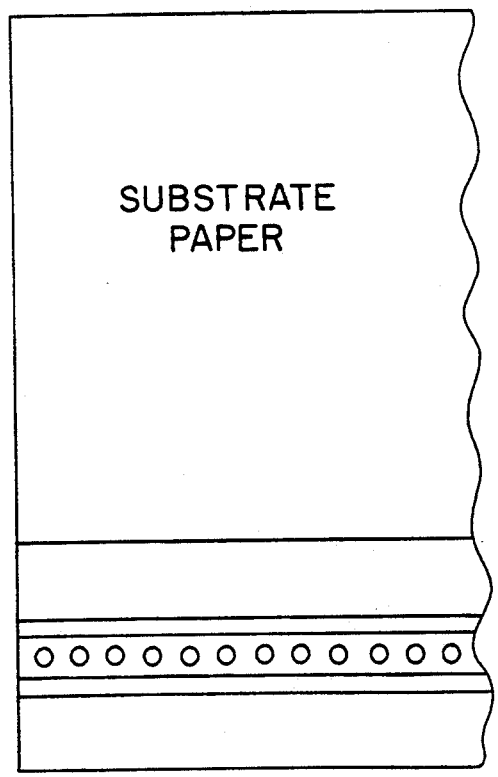
Figure 5C:
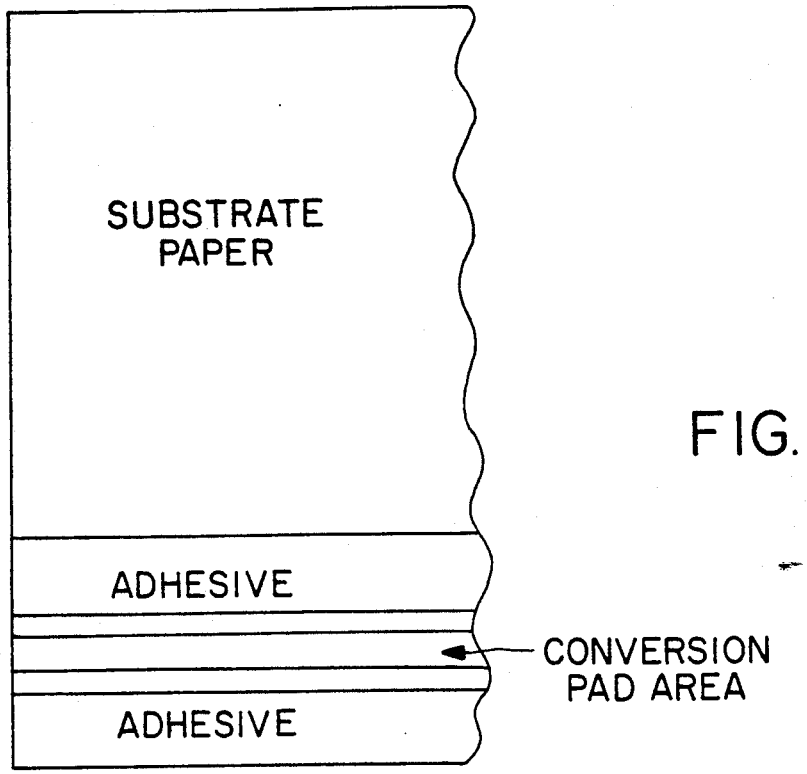
Figure 5D:
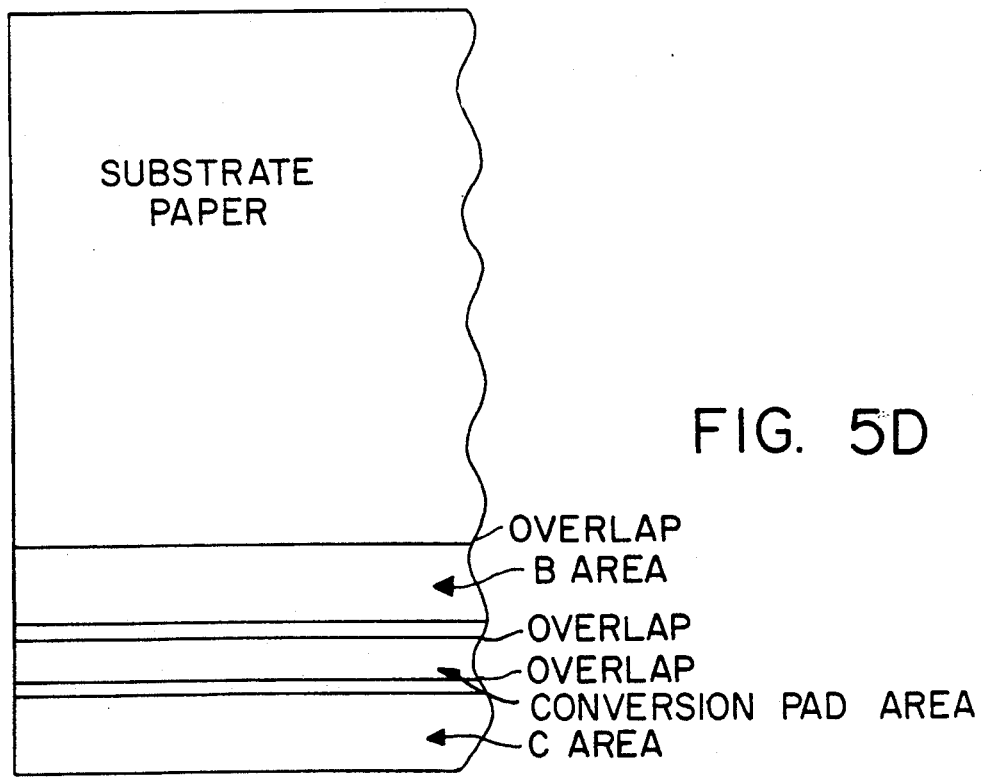
Figure 5E:
Figure 5F:
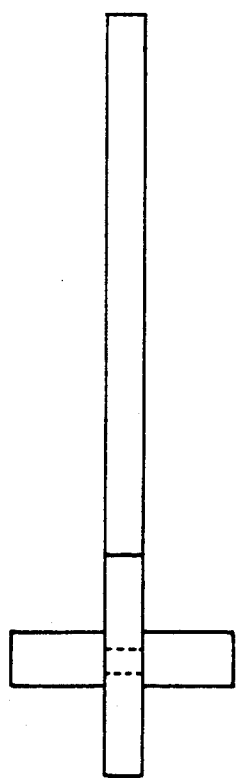

In FIGS. 5a-f are diagrammatically indicated the various stages in preparing a strip. In the first stage, depicted in FIG. 5a, adhesive liner is removed and the adhesive tape exposed on the upper 7 cm of the 20-cm length of plastic support laminate. A 7-cm×20-cm area of chromatography paper with peroxidase substrate immobilized is laminated with even and firm pressure. In FIG. 5b, ⅛-inch diameter holes are punched 5 mm apart on a center 1.5 cm from the base of the strip. In FIG. 5c, the adhesive is then removed from the sample pad area centered 1.5 cm from the bottom of the strip, and a piece of sample pad paper (0.5 cm×20 cm) is laminated in this area with firm, even pressure, overlapping the adhesive layer at its edges. The release liner is then removed and the adhesive in the bridging strip area is exposed (FIG. 5d). A 1.4-cm×20-cm section of chromatography paper is laminated over area B, ensuring a 1-mm overlap at each interface. Then, a 1.3-cm×20-cm section of paper is laminated over area C providing again for the 1-mm overlap at the pad interface. The strips may then be cut using a paper cutter to provide strips 5-mm wide (FIG. 5e). The lower strip is bent to allow a 0.005inch thick clear Mylar ® slide to be inserted or the metering device to be inserted, after which time the strips may be stored in a dessicator (FIG. 5f).

To further demonstrate the invention, strips were prepared as follows for the detection of cholesterol in serum. A sample strip is prepared as follows. The support layer is composed of polystyrene rigid backing material of 0.01 inch thick. The 3M 443 double-stick tape is provided as a first 10 mm strip beginning at one end, followed by a space of 2.5 mm, a second layer of adhesive having a width of 5 mm, followed by a space of 2.5 mm. Finally, the remainder of the support is covered with 3M 415 double-stick adhesive for a width of 80 mm. A 3 mm hole is punched through the support 15 mm from the end in order to provide the sample loading port.

The measurement or quantitation area is prepared by placing a sheet of Whatman 31ET chromatography paper having a width of 70 mm and may be of any convenient length, so that ultimately the strips may be cut from a larger laminated sheet.

A stock solution is prepared for attachment of the dye to the measurement region. Of particular interest is the use of modified N,N-dimethylaniline, which is N-[Ω-1,2-ethylenediamine carboxamido-butyl],N-methylaniline. The dimethylaniline (DMA) derivative is coupled to the paper employing carbonyl diamidazole. The paper is activated by soaking the paper in 0.20 M carbonyldiimidazole in methylene chloride, followed by soaking the paper in 1.5 mg/ml DMA derivative in methylene chloride.

Following the covalent attachment of the dimethylaniline analog, the paper is soaked in a 0.5 mg/ml solution of 3-methyl-2-benzothiazolinone hydrazone (MBTH), although a concentration in the range of 0.1 to 2 mg/ml is useful. Excess solution is wiped off gently by wiping the paper over one edge of a dish, followed by drying the paper in a forced air convention oven at 50° C. for about 25 minutes. The paper is firmly laminated onto the double-stick adhesive layer in the measurement region extending from one end of the support. At the opposite end, the bridging strips are affixed to the support. The first strip beginning at the end is 13 mm long and is affixed at one end along the adhesive and overlaps the sample pad by about 1 mm. The second strip is 14 mm long and overlaps the sample pad by about 1 mm. In addition, the second strip is placed over the second strip of adhesive extending from the sample pad to the measurement area, while overlapping both the measurement region and sample pad by about 1 mm.

The sample pad is conveniently of cellulose chromatography paper, but glass fiber paper, synthetic membrane, or other suitable material may be employed. Conveniently, the pad is 5 mm×5 mm. The sample pad is impregnated with the following solution:

| | |
|---|---|
| Gantrez AN-149 | 0.5% |
| Gum Arabic | 2.0% |
| Sucrose | 5.0% |
| Mega 8* | 0.83% |
| Gelatin | 0.5% |
| Cholesterol Esterase | 9 u/ml |
| Cholesterol Oxidase | 5 u/ml |
| Sodium Cholate | 1.0% |
| Nonidet P-40 | 1.0% |

*Octanoyl-N-methylglucamide (Sigma #03129).

in 0.1 M potassium phosphate, pH 7.0 buffer. The protective slide or metering system is then inserted under the bridging strips. The slide may be 0.005-inch thick Mylar ® sheet of about 8 mm width, or the metering device, comprising an 8-mm wide plastic screen, Tetko Nitex 3-500/49, 500 μm mesh, 390 μm thick, adhered at its ends by means of 3M 415 double-stick adhesive to Whatman 1C absorbant. The exposed side of the absorbant is covered with a protective layer of 3M 845.

Once the sheet has been assembled, the sheet may now be cut into 5-mm strips, so as to provide the final device. In some instances it may be desirable to first prepare the strip before introducing the protective slide. The strip is now ready to be used in an assay.

The assay is performed as follows. A measured sample of serum, 10 μl where the metering device is not employed, is added through the port on the rear of the strip and the sample pad allowed to incubate for 10 min. The protective slide is then removed by sliding sideways and the end of the device is placed into a 13×100 test tube containing 0.5 ml of peroxidase enzyme solution. The solution has 25 μg/ml of horseradish peroxidase, 2.0 mg/ml of bovine gammaglobulin, in 0.1 M sodium phosphate, 0.2 M sodium chloride, pH 7. The solution is allowed to wick to the top of the strip for approximately 10 min. The height of the color band is then measured and compared to a calibration curve which defines the cholesterol level of the serum in mg/dl. The following table indicates the results. In this table, the MBTH substrate is immobilized in the quantitation area at two levels: 0.25 and 0.50 mg/ml. The results shown below demonstrate that the sensitivity of the assay can be adjusted by varying the amount of immobilized indicator.

| | CALIBRATION CURVE OF SERUM WITH $H_2O_2$ SPIKE | |
|---|---|---|
| | Migration Height | |
| mg/dl* | 0.25 mg/ml | 0.5 mg/ml |
| 50 | 10.0 | 5.0 |
| 100 | 23.5 | 16.0 |
| 200 | 38.0 | 29.0 |
| 400 | 52.0 | 43.0 |

*Values expressed as cholesterol equivalents.

It is evident from the above results, that a simple, rapid method and apparatus for use in the method are provided which allows for measurement of a wide variety of analytes without the need for instrumentation. Thus, various techniques may be employed which would otherwise require colorimeters or spectrophotometers, which can now be performed by simply using a dipstick and measuring the height of a color front. By employing various aspects of the subject invention, sharp color fronts can be achieved and samples can be automatically measured, without the intervention of pipettes, syringes, or other fluid measuring means. In addition, high sensitivity can be achieved and a broad dynamic range can be addressed by varying the various reagents on the strip. The method is relatively insensitive to changes in ambient conditions, so that accurate results can be obtained under varying conditions. The dipstick can be relatively easily made, so that economical means for determining analytes can be made available in places other than clinical laboratories, such as doctor's offices, hospitals, and the home.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A dipstick measuring device comprising:
   in a direction of eluent flow,
   a first bibulous bridging strip extending from an immersion end of said device to a sample pad site;
   a sample pad at said sample pad site;
   a second bibulous bridging strip extending from said sample pad site to a measurement region fluid receiving site; and
   an extended bibulous measurement strip in fluid communication with said second bridging strip and impregnated with a first member of a signal producing system, which upon reaction with a second member of said signal producing system produces a detectable signal defining a boundary on said measurement strip; and
   a removable inert protective barrier separating said sample pad from fluid communication with said first and second bridging strips and bringing said sample paid into fluid communication with said first and second bridging strips when removed.

2. A device according to claim 1, wherein said first and second bridging strips overlap said sample pad without contact between said strips.

3. A device according to claim 1, wherein said first and second bridging strips, said sample pad and said bibulous measurement strip are bound to and supported by a supporting film.

4. A device according to claim 1, wherein said signal producing system comprises at least one enzyme impregnated in said sample pad.

5. A device according to claim 4, wherein said enzyme is an oxidase.

6. A dipstick measuring device comprising:
   in a direction of eluent flow;
   a first bibulous bridging strip extending from an immersion end of said device to a sample pad site;
   a sample pad at said sample pad site;
   a second bibulous bridging strip extending from said sample pad site to a measurement region fluid receiving site; and
   an extended bibulous measurement strip in fluid communication with said second bridging strip and impregnated with a first member of a signal producing system, which upon reaction with a second member of said signal producing system produces a detectable signal defining a boundary on said measurement strip; and
   a removable inert protective barrier separating said sample pad from fluid communication with said first and second bridging strips and bringing said sample pad into fluid communication with said first and second bridging strips when removed said sample pad and said bibulous measurement strip are bound to and supported by a supporting film, and said supporting film has a sample port beneath said sample pad.

7. A dipstick measuring device comprising:
   in a direction of eluent flow,
   a first bibulous bridging strip extending from an immersion end of said device to a sample pad site;
   a sample pad at said sample pad site;
   a second bibulous bridging strip extending from said sample pad site to a measurement region fluid receiving site; and
   an extended bibulous measurement strip in fluid communication with said second bridging strip and impregnated with a first member of a signal producing system, which upon reaction with a second member of said signal producing system produces a detectable signal defining a boundary on said measurement strip; and in addition
   a removable inert protective barrier separating said sample pad from fluid communication with said first and second bridging strips and bringing said sample pad into fluid communication with said first and second bridging strips when removed; and a spanning bibulous strip extending from said immersion end to said measurement strip in fluid communication with said measurement strip; and
wherein said second bridging strip has a region narrower than said spanning strip.

8. A device according to claim 7, wherein said spanning bibulous strip intervenes between and provides fluid communication between said second bridging strip and said measurement strip.

9. A device according to claim 7, wherein said narrower region of said second bridging strip is of from about 20 to 80% of the width of said spanning strip.

10. A dipstick measuring device comprising:
in a direction of eluent flow,
a first bibulous bridging strip extending from an immersion end of said device to a sample pad site;
a sample pad at said sample pad site;
a second bibulous bridging strip extending from said sample pad site to a measurement region fluid receiving site; and
an extended bibulous measurement strip in fluid communication with said second bridging strip and impregnated with a first member of a signal producing system, which upon reaction with a second member of said signal producing system produces a detectable signal defining a boundary on said measurement strip; and
a removable metering device comprising a porous non-wetting member in fluid receiving contact with said sample pad, an absorbant layer backing for receiving fluid from said sample pad, covered with an inert film providing an inert protective barrier separating said sample pad from fluid communication with said first and second bridging strips, said removable metering device bringing said sample pad into fluid communication with said first and second bridging strips when removed.

11. A dipstick measuring device comprising:
in a direction of eluent flow;
a first bibulous bridging strip extending from an immersion end of said device to a sample pad site;
a sample at said sample pad site;
a second bibulous bridging strip extending from said sample pad site to a measurement region fluid receiving site;
an extended bibulous measurement strip in fluid communication with said second bridging strip and impregnated with a first member of a signal producing system, which upon reaction with a second member of said signal producing system, produces a detectable signal defining a boundary on said measurement strip; and
a removable metering device comprising a porous; non-wetting member in fluid receiving contact with said sample pad, said porous non-wetting member consisting essentially of a plastic screen of about 250 μm to about 1 mm and a thickness in the range of about 150 to 600 μm, an absorbent layer backing for receiving fluid from said sample pad, covered with an inert film providing an inert protective barrier separating said sample pad from fluid communication with said first and second bridging strips, said removable metering device bringing said sample pad into fluid communication with said first and second bridging strips when removed.

12. A dipstick measuring device comprising:
in a direction of eluent flow,
a first bibulous bridging strip extending from an immersion end of said device to a sample pad site;
a sample pad at said sample pad site;
a second bibulous bridging strip extending from said sample pad site to a measurement region fluid receiving site; and
an extended bibulous measurement strip in fluid communication with said second bridging strip and impregnated with a first member of a signal producing system, which upon reaction with a second member of said signal producing system produces a detectable signal defining a boundary on said measurement strip; and in addition
a spanning bibulous strip extending from said immersion end to said measurement strip in fluid communication with said measurement strip;
wherein said second bridging strip has a region narrower than said spanning strip;
a removable metering device comprising a porous non-wetting member in fluid receiving contact with said sample pad, an absorbant layer backing for receiving fluid from said sample pad, covered with an inert film providing an inert protective barrier separating said sample pad from fluid communication with said first and second bridging strips, and removable metering device bringing said sample pad into fluid communication with said first and second bridging strips when removed.

13. A method for measuring the presence of an analyte in a sample, employing a device comprising a first bridging bibulous member for transferring eluent from a fluid source to a sample pad, a second bridging member for transferring eluent fluid from said sample pad to a measuring extended bibulous strip impregnated with a second member of a signal producing system, said method comprising:
impregnating a sample pad with an assay medium resulting in the presence of a first member of a signal producing system in said sample pad in an amount related to the amount of analyte in said sample, while preventing transport of said assay medium to said bridging bibulous members;
directing an eluent stream from an eluent source to said sample pad to transfer said first member from said pad to said measuring strip through said second bridging member;
directing said first member containing eluent through said measuring strip, whereby said first and second members of said signal producing system and any additional members of said signal producing system react to produce a detectable boundary on said measuring strip, wherein the extent of said is related to the amount of analyte in said sample.

14. A method for measuring the presence of an analyte in a sample, employing a device comprising:
a first bridging bibulous member for transferring eluent from a fluid source to a sample pad;
a second bridging member for transferring eluent fluid from said sample pad to a measuring extended bibulous strip impregnated with a second member of a signal-producing system, said method comprising:
impregnating a sample pad with an assay medium, resulting in the presence of a first member of a signal-producing system in said sample pad in an amount related to the amount of analyte in said sample, while preventing transport of said assay medium to said bridging bibulous members;

directing an eluent stream from an eluent source to said sample pad to transfer said first member from said pad to said measuring strip through said second bridging member;

directing said first member containing eluent through said measuring strip;

directing a diverted stream directly from said eluent source to said measuring member, wherein said diverted stream extends the width of said measuring member and said first member containing eluent stream is narrower than the width of said measuring member and is directed to the middle of said measuring member;

whereby said first and second members of said signal producing system and any additional members of said signal producing system react to produce a detectable boundary on said measuring strip, when the extent of said boundary is related to the amount of analyte in said sample.

15. A method according to claim 14, further comprising;

impregnating said sample pad with a greater than saturating amount of said assay medium; and wicking excess assay medium through a plastic mesh into an absorbant layer; and removing said plastic mesh and absorbant layer from said sample pad prior directing said eluent stream to said sample pad, whereby said assay medium is measured in a reproducible manner.

16. A method according to claim 14, whereby said signal producing system comprises an oxidase covalently immobilized in said sample pad, a dialkylaniline covalently immobilized in said measuring strip, a hydrazine impregnated in said measuring strip and a peroxidase in said eluent.

17. A method according to claim 16, wherein said oxidase is glucose oxidase and said analyte is glucose.

18. A method according to claim 16, wherein said oxidase is alcohol oxidase and said analyte is an alcohol.

19. A method according to claim 16, wherein said oxidase is cholesterol oxidase and said analyte is cholesterol and said signal producing system further comprises cholesterol esterase impregnated in said sample pad.

20. A kit comprising a device according to claim 1, members of said signal producing system, and a sample metering device comprising a wicking mesh backed with an absorbant layer.

21. A kit according to claim 20, wherein said signal producing system comprises horseradish peroxidase.

* * * * *